(12) United States Patent
Skubacz et al.

(10) Patent No.: US 8,463,816 B2
(45) Date of Patent: Jun. 11, 2013

(54) METHOD OF ADMINISTERING A KNOWLEDGE REPOSITORY

(75) Inventors: Michal Skubacz, Gröbenzell (DE); Sonja Zillner, München (DE)

(73) Assignee: Siemens Aktiengesellschaft, Munich (DE)

( * ) Notice: Subject to any disclaimer, the term of this patent is extended or adjusted under 35 U.S.C. 154(b) by 58 days.

(21) Appl. No.: 13/205,135

(22) Filed: Aug. 8, 2011

(65) Prior Publication Data

US 2012/0331014 A1    Dec. 27, 2012

(30) Foreign Application Priority Data

Jun. 27, 2011  (EP) .................................... 11171553

(51) Int. Cl.
*G06F 17/30* (2006.01)

(52) U.S. Cl.
USPC ............... 707/791; 707/601; 707/603; 705/2; 705/37; 705/13; 704/9; 706/45; 706/50; 717/120; 714/48

(58) Field of Classification Search
USPC .................. 707/600, 601, 603, 791; 705/2, 7, 705/8, 14.37, 7.13; 704/9; 717/120; 706/45, 706/50; 714/48
See application file for complete search history.

(56) References Cited

U.S. PATENT DOCUMENTS

| | | | | |
|---|---|---|---|---|
| 5,737,727 A * | 4/1998 | Lehmann et al. | ............ | 705/7.13 |
| 6,907,416 B2 * | 6/2005 | Tasooji et al. | .................. | 706/50 |
| 6,947,917 B1 * | 9/2005 | Mathur et al. | .................. | 706/45 |
| 7,370,004 B1 * | 5/2008 | Patel et al. | ................. | 705/14.37 |
| 7,613,728 B2 * | 11/2009 | Png et al. | ............................. | 1/1 |
| 7,739,230 B2 * | 6/2010 | Bourne et al. | ................... | 707/603 |
| 7,996,814 B1 * | 8/2011 | Qureshi et al. | ............... | 717/120 |
| 8,140,578 B2 * | 3/2012 | Johnson et al. | ............... | 707/791 |
| 2002/0184178 A1 * | 12/2002 | Tasooji et al. | ................... | 706/50 |
| 2003/0004706 A1 * | 1/2003 | Yale et al. | ......................... | 704/9 |
| 2003/0004932 A1 * | 1/2003 | Chow et al. | ....................... | 707/3 |
| 2003/0065663 A1 * | 4/2003 | Chu | ............................... | 707/10 |
| 2003/0144892 A1 * | 7/2003 | Cowan et al. | ..................... | 705/8 |
| 2003/0180766 A1 * | 9/2003 | Farnet et al. | ...................... | 435/6 |
| 2004/0078725 A1 * | 4/2004 | Little et al. | ...................... | 714/48 |
| 2004/0078726 A1 * | 4/2004 | Little et al. | ...................... | 714/48 |
| 2004/0078727 A1 * | 4/2004 | Little et al. | ...................... | 714/48 |
| 2004/0153962 A1 * | 8/2004 | Bazoon | ........................ | 715/500 |
| 2004/0249871 A1 * | 12/2004 | Bazoon | ........................ | 707/206 |
| 2006/0235727 A1 * | 10/2006 | Singer et al. | ..................... | 705/2 |
| 2006/0253495 A1 * | 11/2006 | Png | ................................. | 707/200 |
| 2007/0061084 A1 * | 3/2007 | Farnet et al. | .................... | 702/19 |
| 2007/0094191 A1 * | 4/2007 | Wu et al. | ......................... | 706/46 |
| 2008/0010025 A1 * | 1/2008 | Farnet et al. | ..................... | 702/20 |
| 2008/0077462 A1 * | 3/2008 | Patel et al. | ........................ | 705/7 |
| 2008/0195642 A1 * | 8/2008 | Voln | ................................. | 707/101 |
| 2009/0043825 A1 * | 2/2009 | Bourne et al. | ................. | 707/202 |
| 2009/0119240 A1 * | 5/2009 | Fleming et al. | ................. | 706/46 |
| 2010/0017427 A1 * | 1/2010 | Johnson et al. | ............... | 707/102 |
| 2010/0324927 A1 * | 12/2010 | Tinsley | ............................ | 705/2 |

* cited by examiner

*Primary Examiner* — Frantz Coby

(74) *Attorney, Agent, or Firm* — King & Spalding L.L.P.

(57) ABSTRACT

The method of administering a knowledge repository described herein establishes combining data input with concurrent data analytics in order to improve the quality and relevance of data entries.

9 Claims, 3 Drawing Sheets

FIG 1   STATE OF THE ART

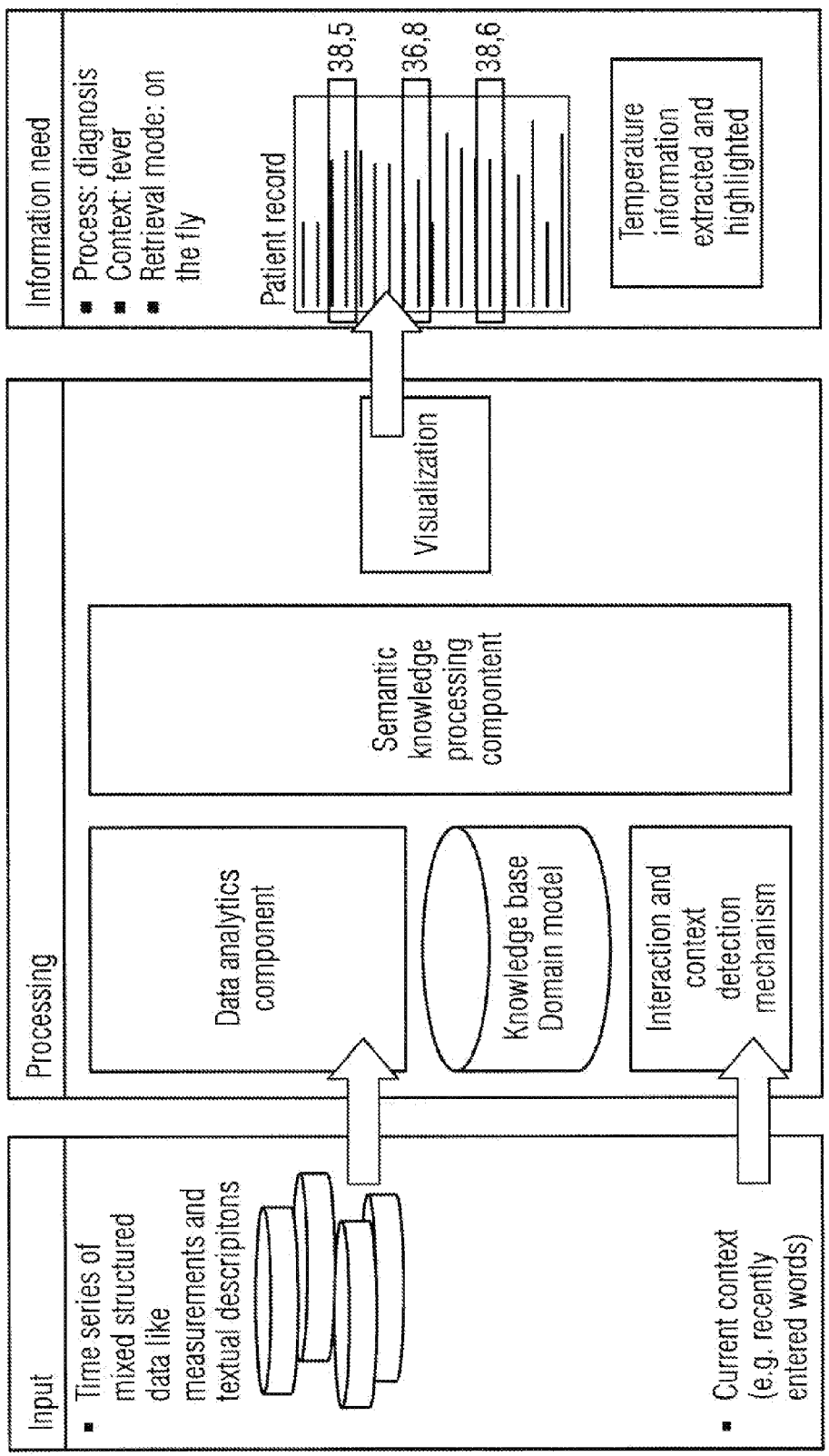

METHOD OF ADMINISTERING A KNOWLEDGE REPOSITORY

CROSS-REFERENCE TO RELATED APPLICATIONS

This application claims priority to EP Patent Application No. 11171553 filed Jun. 27, 2011. The contents of which is incorporated herein by reference in its entirety.

TECHNICAL FIELD

The invention provides a method for administering a knowledge repository.

BACKGROUND

Knowledge repositories, such as personal patient data records or service history logs of industrial automation systems, are known in the art.

A knowledge repository allows a user or a machine to input or to amend data into an information object of the repository. An information object of the knowledge repository is added by entering textual data in a textual input module. The information may be amended by a time stamp indicating the point of time the information object was added or amended. A time aspect as well as development and changes over time determine relevance and meaning of single information objects.

Further on, a knowledge repository allows for searching data entries in information objects for the purpose of analyzing an overall situation or drawing a conclusion for a particular problem. Therefore, the sound interpretation of a single data entry requires the reflection of how this information of the data entry relates to proceeding or succeeding information objects.

Commonly known methods of administering such knowledge repositories are generally confronted with the challenge of managing, storing and accessing heterogeneous and time-dependent information objects ranging from time series of mixed data like measurements to textual descriptions.

Commonly known methods of administering knowledge repositories require a high degree of user interaction in evaluating a relation between an actual text entry and past information objects. In addition, the processing and assessment of time series of information objects is cumbersome, as the relation between information objects of different points in time cannot be inferred comprehensively. On the contrary, an assessment of the relation between information objects requires in-depth human assessment.

SUMMARY

According to various embodiments, a method for administering a knowledge repository can be provided which allows for an improved assessment between an actual text entry and past information objects.

According to an embodiment, a method of administering a knowledge repository, the knowledge repository comprising a plurality of information objects, at least one of said information objects including at least one text element, may comprise the steps of:—providing at least one knowledge base from a memory unit, the knowledge base including a plurality of concepts and a plurality of relationship between said plurality of concepts;—providing a data analytics module, the data analytics module assigning at least one of said plurality of concepts and/or at least one of said plurality of relationships to at least one text element of at least one of said plurality of information objects; providing a semantic knowledge processing component, the semantic knowledge processing component calculating a type and degree of at least one of said plurality of relationships between concepts assigned to at least one text element of at least one of said plurality of information objects; providing a textual input module, the textual input module being adapted to amend or add one of said plurality of information objects by at least one input text element; providing a display module, the display module being adapted to display a list of information objects included in said knowledge repository, each information object being displayed by a caption of said information object; providing an interaction module, the interaction module emphasizing at least one information object in the display module, each of at least one emphasized information object having a semantic relationship with the contents of said textual input module, the semantic relationship being inferred by said type and degree of relationship; and;—providing an annotation module, the annotation module linking one of said input text element by a reference to an emphasized information object.

According to a further embodiment, said knowledge base can be formed by at least one of a group of resources, the group of resources including a taxonomy, a thesaurus, an ontology, a dictionary, a set of keywords or a lexicon. According to a further embodiment, each of at least one emphasized information object may have a context-relevant relationship with the contents of said textual input module, the context-relevant relationship being inferred by said type and degree of relationship.

According to another embodiment, a computer program product, which contains a program code stored on a computer-readable medium and which, when executed on a computer, may carry out a method as described above.

According to yet another embodiment, a system for administering a knowledge repository, may comprise:—a knowledge base including a plurality of concepts and a plurality of relationship between said plurality of concepts;—a data analytics module for assigning at least one of said plurality of concepts and/or at least one of said plurality of relationships to at least one text element of at least one of said plurality of information objects;—a semantic knowledge processing component for calculating a type and degree of at least one of said plurality of relationships between concepts assigned to at least one text element of at least one of said plurality of information objects;—a textual input module being adapted to amend or add one of said plurality of information objects by at least one input text element;—a display module being adapted to display a list of information objects included in said knowledge repository, each information object being displayed by a caption of said information object;—an interaction module for emphasizing at least one information object in the display module, each of at least one emphasized information object having a semantic relationship with the contents of said textual input module, the semantic relationship being inferred by said type and degree of relationship; and;—an annotation module for linking one of said input text element by a reference to an emphasized information object.

BRIEF DESCRIPTION OF THE DRAWINGS

Various embodiments as well as further advantages will become more apparent and readily appreciated from the following description, taken in conjunction with the accompanying drawing of which:

FIG. 3 shows a structural view of functional components according to an embodiment;

DETAILED DESCRIPTION

Figure 1:
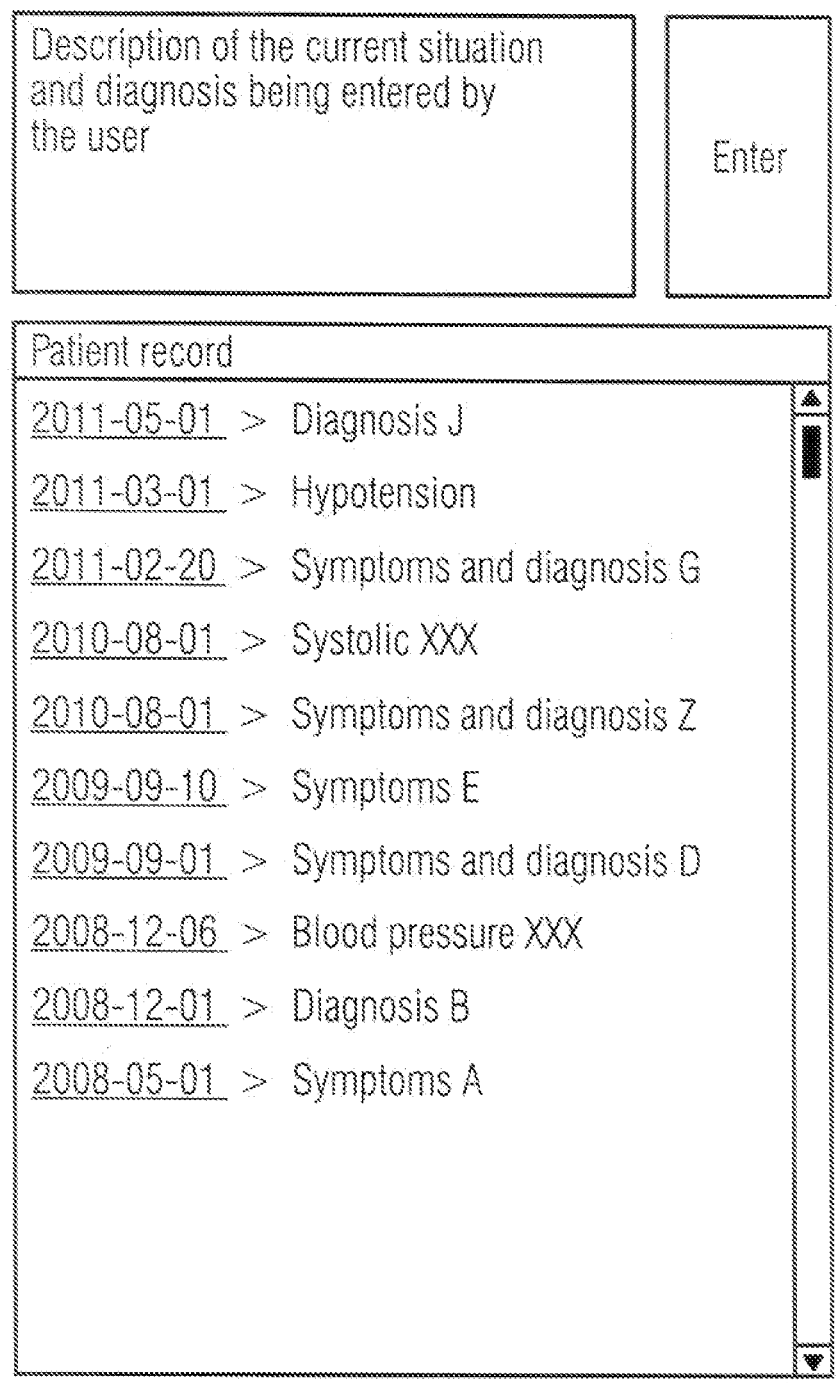
FIG. 1 shows a known user interface for administering a knowledge repository, including a textual input module and a display module.

According to various embodiments, a method of administering a knowledge repository can be provided, the knowledge repository comprising a plurality of information objects, at least one of said information objects including at least one text element, said method comprising the steps of:

providing at least one knowledge base from a memory unit, the knowledge base including a plurality of concepts and a plurality of relationship between said plurality of concepts;

providing a data analytics module, the data analytics module assigning at least one of said plurality of concepts and/or at least one of said plurality of relationships to at least one text element of at least one of said plurality of information objects;

providing a semantic knowledge processing component, the semantic knowledge processing component calculating a type and degree of at least one of said plurality of relationships between concepts assigned to at least one text element of at least one of said plurality of information objects;

providing a textual input module, the textual input module being adapted to amend or add one of said plurality of information objects by at least one input text element;

providing a display module, the display module being adapted to display a list of information objects included in said knowledge repository, each information object being displayed by a caption of said information object;

providing an interaction module, the interaction module emphasizing at least one information object in the display module, each of at least one emphasized information object having a semantic relationship with the contents of said textual input module, the semantic relationship being inferred by said type and degree of relationship; and;

providing an annotation module, the annotation module linking one of said input text element by a reference to an emphasized information object.

The data analytics module, the textual input module, the display module, the interaction module, and the annotation module comprise any suitable hardware and software, including computer instructions stored in non-transitory computer-readable media and executable by at least one processor to perform the corresponding functions of each module discussed herein.

The proposed method establishes a mechanism that is capable of emphasizing relevant historical information objects helping an expert or a user to adjust or to fine-tune currently entered data as well as to analyze the relevance of the currently entered data in comparison to an overall situation reflected by historical information objects.

Thus, the proposed method advantageously supports conclusions for of the expert, for example in a diagnosis of human diseases or a technical system failure. The emphasizing is effected concurrently to the process of entering data.

The proposed method is driven by the idea to efficiently use the time of an expert user when she or he is available to the knowledge repository, i.e. at the time when he/she is entering new data.

Thus, the proposed method allows the expert user—while she or he is entering new data—to navigate to historical but related information objects and, thus, develop a comprehensive view of the data set in terms of progress over time.

To this end, an interaction module is provided which is effecting an emphasis of at least one information object in a display module.

For this purpose, the interaction module determines a semantic relationship of the contents of a currently typed textual content, which is input by an input module, and the contents of historical information objects. The semantic relationship is inferred by a previously determined type and degree of relationship in view of the information objects.

By learning about historical information objects, the expert user is able to fine-tune the data entry and to relate or link a currently typed textual content to past historical information objects. This link is provisioned by an annotation module, which links an input text element, i.e. a subset of a currently typed textual content, a paragraph of a document, etc., by a reference to an emphasized information object.

In this way, the proposed method establishes a mechanism that combines data input with data analytics in order to improve the quality and relevance of new data entries as well as the analytical process as such.

Advantageously, the user is pointed to other information objects which she or he should consider before making any decision, which may be a diagnosis towards a disease. In this way, the likelihood of a wrong decision decreases.

Examples of experts using the knowledge repository are medical doctors entering information about currently detected symptoms with the system emphasizing history of the same or related symptoms or related disease. A further example is a service technician entering information about visible faults of a machine into another kind of knowledge repository, the knowledge repository emphasizing historical information objects including of same faults or including information about the grounds of faults related to the actual fault.

Another advantage of the proposed method lies in the fact that by means of an intelligent user interaction mechanism data analytics are accomplished while users are providing new information to the systems.

FIG. 1 shows a known user interface for administering a knowledge repository, including a textual input module and a display module.

According to FIG. 1, a user interface for administering a knowledge repository is provided, the knowledge repository adapted to administrate patient records.

A first input control element interworking with a—not shown—textual input module of the knowledge repository is arranged at the upper left of the user interface. By this input control element a free-form text (in the drawing exemplarily captioned as >>Description of the current situation and diagnoses being entered by the user<<) may be entered into a newly created information object, or, alternatively, added to an existing information object.

The textual input is effected by a second control element, namely a button captioned >>Enter<< adjacent to the right boarder of the input module.

A third control element is interworking with a—not shown—display module of the knowledge repository and showing a list of information objects included in said knowledge repository. The information objects shown in FIG. 1 are ordered in a chronological order. Each information object is characterized by a time stamps, e.g. >>2011-05-01<< and a caption of the information object, e.g. >>Diagnosis J<<. The third control element is captioned by >>Patient Record<<, indicating that the respective repository contains information objects related to a patient record.

Figure 2:
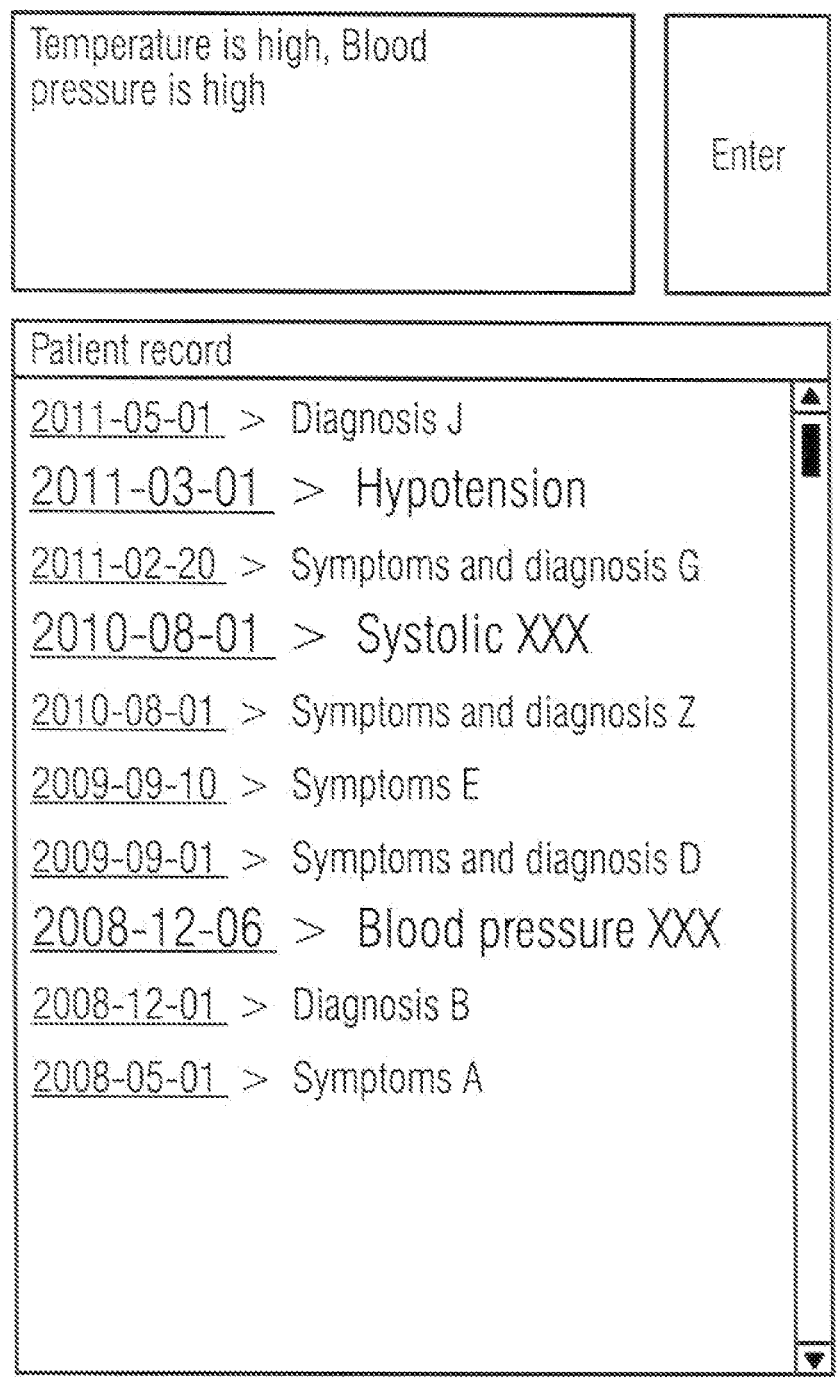
FIG. 2 shows a user interface according to a possible embodiment.

FIG. 2 shows a user interface according to a possible embodiment.

In general accordance with FIG. 1, a user interface for administering a knowledge repository, which is improved by means of the proposed method, is shown in FIG. 2.

According to FIG. 2, a currently typed diagnosis >>Temperature is high, Blood Pressure is high<< is entered into the input control element.

While this diagnosis is entered to the knowledge repository, related information objects in the display control element related to the display module are emphasized by magnifying or, alternatively, by highlighting the captions of the respective information elements.

The sound interpretation of a single data entry requires the reflection of how this data entry relates to preceding or succeeding information objects. By capturing the semantic relations and contexts between the information objects having different timestamps, data access becomes more efficient, accurate and intelligent.

According to the proposed method an expert is able to analyze the existing data sources (time series of data) while entering a new information object.

By evaluating contents of a new entry, related information objects are emphasized to the expert. In other words, meanwhile entering new data, the expert is able to learn about related historical information objects and, at the same time, about the relevance of currently entered data.

By emphasizing context-relevant historical information objects, the expert is able to re-think and re-interpret the relevance and meaning of the new information as well as to avoid adding redundant information to the knowledge repository.

Thus, she or he can decide to refine currently entered data entry accordingly, i.e. amending the contents, or to add a link between the currently entered data entry to historical information objects by formally capturing the semantic relationship between information objects.

The process of linking is effected by a—not shown—annotation module, the annotation module linking one of said input text element by a reference to an emphasized information object.

The method of administering a knowledge repository described herein establishes means for combining data input with concurrent data analytics in order to improve the quality and relevance of data entries.

FIG. 3 shows a structural view of functional components according to an embodiment.

According to a course structure three categories are distinguished, namely Input, Processing and Information Need.

As to the input portion of the structural view, a time series of mixed structured data like measurements and textual descriptions are depicted in a heap of slices. These slices correspond to the historical information objects, whose captions are shown in the list of the display control element according to FIG. 2. Further on, currently entered data (or a current context, e.g. recently entered words) are structured within the input portion.

The processing or the information objects is provisioned by a data analytics component, hereinafter also referred to as data analytics module.

The data analytics module is processing the information objects and identifies contained concepts and relations between information objects using a knowledge base (or domain model), which is also shown as a part of the processing section. In real implementations, however, this knowledge base may be stored in a decentralised manner.

The knowledge base or domain model contains information about concepts relevant in the domain of concern as well as relations between those concepts. This knowledge base could e.g. contain information about human diseases, their symptoms and human anatomy.

The data analytics component is processing the historical objects and identifies contained concepts and relations between them using the knowledge base/domain model. The data analytics module assigns concepts and relationships to at least one text element contained in an information objects. This operation allows cleaning, transforming and annotating historical information objects with the goal of emphasizing useful information, of suggesting conclusions and thus supporting efficient data entry.

A semantic knowledge processing component calculates a type and degree of relation between concepts assigned to a text element of information objects. This applies to the historical information objects as well as to currently edited text. For this purpose the semantic knowledge processing component is integrating the knowledge base and calculating the strength of relation between directly and indirectly related concepts under consideration of the type of the relation and relation distance.

A user interaction and context detection mechanism, hereinafter also referred to as interaction module, triggers the knowledge repository system to emphasize historical information objects related to a currently data entry. The interaction module interprets the user actions and the entered data and identifies the current user context or interests. Hereby a passive and an active trigger is provided according to alternative embodiments:

The passive trigger automatically processes the data entry of a user. Relating to the latest actions and/or data entries of the user, the system emphasizes corresponding information objects. For instance, the system can automatically highlight any historical data entry that is related especially to the last three words the user typed into the systems.

The active trigger analyzes data entries when this action is actively triggered by the user. In other words, the active trigger provides the user means to actively guide the system in finding and highlighting relevant historical information objects related to the current context. For instance, by marking selected terms of a current data entry text or by dedicated search for terms, the knowledge repository system displays the related information objects.

In summary, the proposed method combines the following technologies:

Data analysis technology is used to detect concepts in historical information objects;

Current context detection technology is used to recognize current user interest. By being able to instantly studying related (historical) data entries, the user can manually fine-tune as well as semantically relate the current data entry to past data entries;

A user interaction mechanism automatically provides a user with related historical information. In addition, the proposed method implements means that allow the user to actively and self-determined search for related information assets, that help the user in fine-tuning and refining the current data entry.

A semantic knowledge processing unit allows to capture semantic relationships between information objects (data entries) over time and to infer implicit additional knowledge.

The proposed method can be implemented in form of a separate application or as a part of a complex system. The implementation can be realized on any system ranging from personal computers to mobile devices with the special focus on dedicated mobile healthcare and service support devices.

What is claimed is:

1. A method of administering a knowledge repository, the knowledge repository comprising a plurality of information objects, at least one of said information objects including at least one text element, said method comprising the steps of:
   providing at least one knowledge base from a memory unit, the knowledge base including a plurality of concepts and a plurality of relationship between said plurality of concepts;
   providing a data analytics module, the data analytics module assigning at least one of at least one of said plurality of concepts and at least one of said plurality of relationships to at least one text element of at least one of said plurality of information objects;
   providing a semantic knowledge processing component, the semantic knowledge processing component calculating a type and degree of at least one of said plurality of relationships between concepts assigned to at least one text element of at least one of said plurality of information objects;
   providing a textual input module, the textual input module being adapted to amend or add one of said plurality of information objects by at least one input text element;
   providing a display module, the display module being adapted to display a list of information objects included in said knowledge repository, each information object being displayed by a caption of said information object;
   providing an interaction module, the interaction module emphasizing at least one information object in the display module, each of at least one emphasized information object having a semantic relationship with the contents of said textual input module, the semantic relationship being inferred by said type and degree of relationship; and;
   providing an annotation module, the annotation module linking one of said input text element by a reference to an emphasized information object.

2. The method according to claim 1, wherein said knowledge base is formed by at least one of: a group of resources, and the group of resources including a taxonomy, a thesaurus, an ontology, a dictionary, a set of keywords, or a lexicon.

3. The method according to claim 1, wherein each of at least one emphasized information object having a context-relevant relationship with the contents of said textual input module, the context-relevant relationship being inferred by said type and degree of relationship.

4. A computer program product comprising a non-transitory computer-readable medium storing a program code which when executed on a computer provides for:
   providing at least one knowledge base from a memory unit, the knowledge base including a plurality of concepts and a plurality of relationship between said plurality of concepts;
   providing a data analytics module, the data analytics module assigning at least one of at least one of said plurality of concepts and at least one of said plurality of relationships to at least one text element of at least one of said plurality of information objects;
   providing a semantic knowledge processing component, the semantic knowledge processing component calculating a type and degree of at least one of said plurality of relationships between concepts assigned to at least one text element of at least one of said plurality of information objects;
   providing a textual input module, the textual input module being adapted to amend or add one of said plurality of information objects by at least one input text element;
   providing a display module, the display module being adapted to display a list of information objects included in said knowledge repository, each information object being displayed by a caption of said information object;
   providing an interaction module, the interaction module emphasizing at least one information object in the display module, each of at least one emphasized information object having a semantic relationship with the contents of said textual input module, the semantic relationship being inferred by said type and degree of relationship; and;
   providing an annotation module, the annotation module linking one of said input text element by a reference to an emphasized information object.

5. The computer program product according to claim 4, wherein said knowledge base is formed by at least one of: a group of resources, and the group of resources including a taxonomy, a thesaurus, an ontology, a dictionary, a set of keywords, or a lexicon.

6. The computer program product according to claim 4, wherein each of at least one emphasized information object having a context-relevant relationship with the contents of said textual input module, the context-relevant relationship being inferred by said type and degree of relationship.

7. A system for administering a knowledge repository, the system comprising:
   a knowledge base including a plurality of concepts and a plurality of relationship between said plurality of concepts;
   a data analytics module for assigning at least one of: at least one of said plurality of concepts and at least one of said plurality of relationships to at least one text element of at least one of said plurality of information objects;
   a semantic knowledge processing component for calculating a type and degree of at least one of said plurality of relationships between concepts assigned to at least one text element of at least one of said plurality of information objects;
   a textual input module being adapted to amend or add one of said plurality of information objects by at least one input text element;
   a display module being adapted to display a list of information objects included in said knowledge repository, each information object being displayed by a caption of said information object;
   an interaction module for emphasizing at least one information object in the display module, each of at least one emphasized information object having a semantic relationship with the contents of said textual input module, the semantic relationship being inferred by said type and degree of relationship; and;
   an annotation module for linking one of said input text element by a reference to an emphasized information object.

8. The system according to claim 7, wherein said knowledge base is formed by at least one of: a group of resources, and the group of resources including a taxonomy, a thesaurus, an ontology, a dictionary, a set of keywords, or a lexicon.

9. The system according to claim 7, wherein each of at least one emphasized information object having a context-relevant relationship with the contents of said textual input module, the context-relevant relationship being inferred by said type and degree of relationship.

* * * * *